(12) United States Patent
Feng et al.

(10) Patent No.: US 7,186,873 B2
(45) Date of Patent: *Mar. 6, 2007

(54) MANUFACTURE OF XYLENES BY REACTIVE DISTILLATION OF REFORMATE

(75) Inventors: Xiaobing Feng, Houston, TX (US); John Scott Buchanan, Lambertville, NJ (US); Robert A. Crane, Lumberton, TX (US); Jihad M. Dakka, Whitehouse Station, NJ (US); Larry L. Iaccino, Friendswood, TX (US); Gary D. Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/465,450

(22) Filed: Jun. 18, 2003

(65) Prior Publication Data

US 2005/0075524 A1 Apr. 7, 2005

Related U.S. Application Data

(60) Provisional application No. 60/389,979, filed on Jun. 19, 2002.

(51) Int. Cl.
*C07C 2/66* (2006.01)
(52) U.S. Cl. ...................... 585/467; 585/446

(58) Field of Classification Search ............... 585/467, 585/446
See application file for complete search history.

(56) References Cited

U.S. PATENT DOCUMENTS

| 4,002,697 | A | | 1/1977 | Chen |
| 4,377,718 | A | * | 3/1983 | Sato et al. .................. 585/467 |
| 4,975,178 | A | * | 12/1990 | Clem et al. .................. 208/65 |
| 5,118,896 | A | | 6/1992 | Steigelmann et al. ....... 585/467 |
| 5,865,986 | A | | 2/1999 | Buchanan et al. ............ 208/65 |
| 5,998,686 | A | * | 12/1999 | Clem et al. .................. 585/415 |
| 7,060,644 | B2 | | 6/2006 | Ghosh et al. |
| 2005/0154242 | A1 | | 7/2005 | Ghosh et al. |

FOREIGN PATENT DOCUMENTS

| WO | WO 98/09928 | 3/1998 |
| WO | WO 99/38823 | 8/1999 |
| WO | WO 01/32591 | 5/2001 |

* cited by examiner

*Primary Examiner*—Thuan Dinh Dang
(74) *Attorney, Agent, or Firm*—Xiaobing Feng

(57) ABSTRACT

A process is provided for the production of xylenes from reformate by reactive distillation. The process is carried out by methylating the benzene/toluene present in the reformate in a reactive distillation zone and under reactive distillation conditions to produce a resulting product having a higher xylenes content than the reformate. Greater than equilibrium amounts of para-xylene can be produced by the process.

41 Claims, 3 Drawing Sheets

MANUFACTURE OF XYLENES BY REACTIVE DISTILLATION OF REFORMATE

CROSS-REFERENCE TO RELATED APPLICATIONS

This application claims priority to U.S. Provisional Patent Application No. 60/389,979, filed Jun. 19, 2002, which is hereby incorporated by reference.

BACKGROUND OF THE INVENTION

1. Field of the Invention

This invention relates to a process for producing xylenes from reformate by methylating the benzene and/or toluene present in the reformate under reactive distillation conditions to produce xylenes.

2. Description of the Prior Art

Most aromatics production is based on the recovery of aromatics derived from catalytic reforming of naphtha. That process, using a feed containing a $C_6+$ hydrocarbons, typically produces a reformate comprised of $C_6$–$C_8$ aromatics along with paraffins and heavier aromatics.

Aromatics can also be produced by the dehydrocyclo-oligomerization of $C_2$–$C_5$ aliphatic hydrocarbons. That process typically produces a product comprised of benzene, toluene, xylenes, $C_5+$ paraffins, $C_{4-}$ light paraffins, olefins, and unreacted $C_2$–$C_5$ aliphatic hydrocarbons.

Another technique for producing aromatics involves the cracking of hydrocarbons such as by steam cracking or catalytic cracking. That process typically produces a product comprised of benzene, toluene, xylenes, $C_6+$ paraffins, and other hydrocarbons.

The aromatics present in the reformate stream from a reformer or cracker will depend on the composition of the feedstock to the reformer or cracker, the type of reformer or cracker, and the operating conditions of the reformer or cracker. Normally, the aromatics present in the reformate stream will comprise benzene, toluene, a near equilibrium mixture of xylenes, ethylbenzene, and a mixture of nominally of $C_9$–$C_{10}$. Products of the reformate having the most value are benzene and xylenes. Of the xylene isomers, i.e., ortho-, meta- and para-xylene, the para-xylene is of particular value as a large volume chemical intermediate in a number of applications, such as the manufacture of terephthalic acid, which is an intermediate in the manufacturer of polyester.

The reformate is usually sent to an aromatics recovery complex where it undergoes several processing steps in order to recover high value products, e.g., xylenes and benzene, and to convert lower value products, e.g., toluene, into higher value products. For example, the aromatics present in the reformate are usually separated into different fractions by carbon number; e.g. benzene, toluene, xylenes, and ethylbenzene, etc. The $C_8$ fraction is then subjected to a processing scheme to make more high value para-xylene. Para-xylene is usually recovered in high purity from the $C_8$ fraction by separating the para-xylene from the ortho-xylene, meta-xylene, and ethylbenzene using selective adsorption or crystallization. The ortho-xylene and meta-xylene remaining from the para-xylene separation are isomerized to produce an equilibrium mixture of xylenes. The ethylbenzene is isomerized into xylenes or is dealkylated to benzene and ethane. The para-xylene is then separated from the ortho-xylene and the meta-xylene using adsorption or crystallization and the para-xylene-deleted-stream is recycled to extinction to the isomerization unit and then to the para-xylene recovery unit until all of the ortho-xylene and meta-xylene are converted to para-xylene and recovered.

Toluene is typically recovered as a separate fraction and then may be converted into higher value products, e.g., benzene and/or xylenes. One toluene conversion process involves the disproportionation of toluene to make benzene and xylenes. Another process involves the hydrodealkylation of toluene to make benzene.

Both toluene disproportionation and toluene hydrodealkylation result in the formation of benzene. With the current and future anticipated environmental regulations involving benzene, it is desirable that the toluene conversion not result in the formation of significant quantities of benzene.

Xylenes can be produced by the methylation of toluene. One advantage of producing xylenes by this process is that the xylenes production does not result in the formation of benzene by-product. Such a process, as disclosed in U.S. Pat. No. 4,002,697, involves the methylation of toluene in the presence of an aluminosilicate zeolite such as ZSM-5. In order to reduce the amount of undesirable methylating agent/methylating agent and methylating agent/xylene reactions, the process can be carried out within a fixed bed reactor and with an excess of toluene at temperatures exceeding 400° C. However, when the process is carried out at these temperatures, a considerable amount of undesirable by-products can also be formed. For instance, at reaction temperatures greater than 400° C., methanol may form undesirable amounts of dimethyl-ether, $C_9^+$ aromatics, and $C_5-$ by-products. Also, carrying out toluene methylation at these temperatures can result in the disproportionation of toluene with the resultant production of benzene. Further $C_5+$ paraffins can be cracked to form $C_{5-}$ paraffins. If the temperature used to carry out the process in the fixed bed reactor is reduced to 400° C. or less, the amount of toluene converted to xylenes can be substantially reduced.

In the past when it was desirable to methylate toluene, toluene present in the reformate has usually been first separated from the other hydrocarbons present in the reformate, such as by fractionation and extraction, before entering a methylation reactor. Such a separation can require a substantial capital investment in equipment, e.g., heat exchangers, high pressure separator, fractioners, etc. In addition, the reformate leaving the reformer is at elevated temperature and highly suitable for further conversion. With the separation of toluene from the reformate, the recovered toluene must be heated again to conversion temperatures.

The present invention is directed to a process for producing xylenes from reformate by toluene methylation which can result in high toluene and/or benzene conversion to xylenes with reduced by-product formation.

SUMMARY OF THE INVENTION

In accordance with the present invention, there is provided a process for producing xylenes from reformate, which process comprises:

(a) providing a reformate containing benzene, toluene or mixtures thereof; and, (b) methylating at least a portion of the benzene, toluene, or mixtures thereof present in said reformate in a reactive distillation zone with a methylating agent under reactive distillation conditions and in the presence of a catalyst effective for the methylation to produce a resulting product having a higher xylenes content than said reformate.

In another embodiment, there is provided a process for producing xylenes from reformate formed in an aromatization zone, which process comprises:

(a) forming reformate containing benzene, toluene or mixtures thereof in an aromatization zone;

(b) transferring at least a portion of the reformate from said aromatization zone to a reactive distillation zone; and, (c) methylating at least a portion of the benzene, toluene, or mixtures thereof present in said reformate in a reactive distillation zone with a methylating agent under reactive distillation conditions and in the presence of a catalyst effective for the methylation to produce a resulting product having a higher xylenes-content than said reformate.

In a further embodiment, there is provided a multistage integrated process for upgrading a petroleum naphtha which comprises the steps of:

(a) introducing the naphtha to an aromatization zone;

(b) reforming the naphtha under aromatization conditions and the presence of a catalyst effective for the aromatization of the naphtha to produce a reformate containing benzene, toluene or mixtures thereof;

(c) transferring at least a portion of the reformate from said aromatization zone to a reactive distillation zone; and, (d) methylating in a reactive distillation zone at least a portion of the benzene, toluene or mixtures thereof present in said reformate with a methylating agent under reactive distillation conditions and in the presence of a catalyst effective for the methylation to produce a resulting product having a higher xylenes content than said reformate.

In carrying out the process of the present invention, substantial amounts of xylenes, including para-xylene, can be produced, while at the same time, the formation of undesirable by-products can be reduced. Also, another important feature of the present invention is that the aromatization zone and reactive distillation zone can be in series flow arrangement, with or without intermediate separation of the reformate.

The methylation reaction can occur in the liquid phase or the vapor phase. Usually the reaction will occur in the vapor phase. The presence of the vapor phase in the reactor zone results in increased catalytic activity in the reactor zone and increased diffusion of molecules to the catalytic sites of the catalyst, e.g., pores of the molecular sieve. The expression "vapor phase", as used herein, includes the presence of minor amounts of some liquid phase, e.g., less than 10 percent by volume of liquid, as well as the substantial absence of liquid phase.

DETAILED DESCRIPTION OF THE INVENTION

The term "aromatization", as used herein, shall mean the production of aromatics comprising benzene, toluene, or mixtures thereof by the conversion of non-aromatic hydrocarbons to aromatic hydrocarbons comprising benzene, toluene, or mixtures thereof. The term "aromatization", as used herein, shall also include the production of aromatics comprising benzene, toluene, or mixtures thereof by the cracking of heavy aromatic hydrocarbons to produce the aromatic hydrocarbons comprising benzene, toluene, or mixtures.

Examples of aromatization processes include catalytic reforming of naphtha, dehydrocyclo-oligomerization of $C_2$–$C_5$ aliphatic hydrocarbons, steam cracking of hydrocarbons to produce aromatic hydrocarbons comprising benzene, toluene, or mixtures thereof, and the catalytic cracking of hydrocarbons to produce aromatic hydrocarbons comprising benzene, toluene, or mixtures thereof.

The term "reformate", as used herein, shall mean the product produced by "aromatization".

Figure 1:
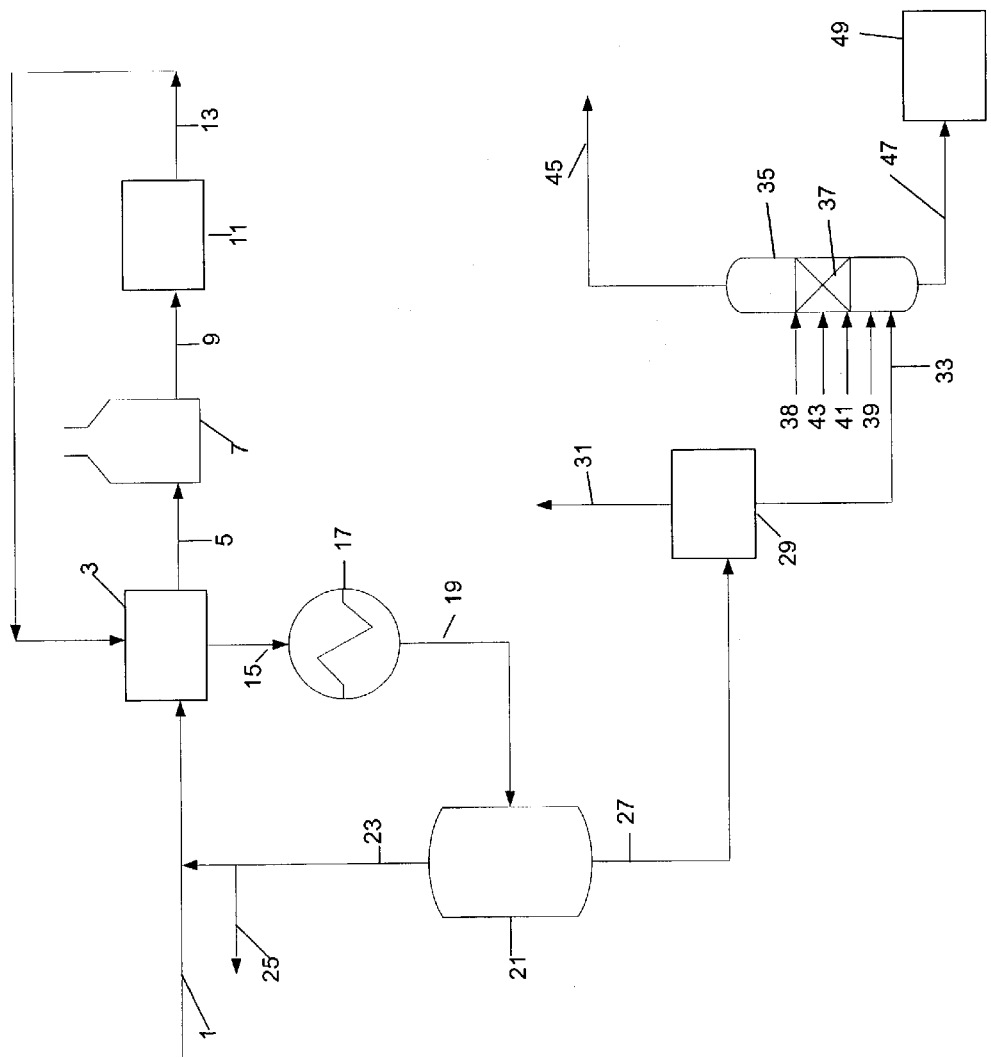
FIG. 1 is a simplified process flow diagram, illustrating an embodiment of the invention.

FIG. 1 is a simplified schematic flow diagram of the invention where the methylation reaction is carried out in a reactive/distillation column located outside of the reforming loop. Referring to FIG. 1, naphtha is directed via line 1 to heat exchanger 3 where the temperature of the naphtha is elevated. The naphtha feed can be either naphtha alone or the naphtha can be combined with toluene. Next, the heated naphtha is sent via line 5 to reformer heater 7 which elevates the temperature of the feed to a temperature suitable for reforming. After heating, the naphtha is withdrawn via line 9 to aromatization reactor zone 11 where the naphtha is reformed into aromatic products. Although only one reactor zone is shown, there can be more than one reactor zone. The reformate is then withdrawn and sent via line 13 to heat exchanger 3. Heat exchanger 3 cools the reformate and uses heat recovered from the reformate to elevate the temperature of the naphtha supplied via line 1. Next, the reformate is withdrawn through line 15 to heat exchanger 17 to further cool the reformate for separation of hydrogen from the product. Next, the cooled reformate is sent via line 19 to high pressure separator 21 where hydrogen is recovered. Hydrogen is removed via line 23 and either recycled back to the reforming unit or removed from the system via line 25. Next, the product is sent via line 27 to separation block 29 where low pressure hydrogen, $C_{4-}$ and $C_5$ are separated and removed via line 31. The resulting product, primarily $C_{6+}$, including benzene and toluene, is supplied via line 33 to reactive distillation column 35. In reactive distillation column 35, the toluene present in the reformate is methylated to form xylenes. Also, benzene present in the reformate can be methylated to form toluene which, in turn, can be methylated to form xylenes. If desired, a stream of hydrocarbons comprised of benzene and/or toluene can be added to the reformate or supplied directly to reactive distillation column 35, such as through inlet 38. The methylation reaction can be carried out in the vapor phase. When carried out in the vapor phase, the reformate can be heated either before it enters the methylation reaction zone or after it has entered the methylation reaction zone. Reactive/distillation column 35 is provided with reaction section 37, inlets for the methylating agent feed, 39, 41, and 43, column overhead outlet line 45 where $C_6/C_7$, including benzene and toluene, are removed overhead via line 45 for further processing and column bottoms outlet line 47 where the $C_{8+}$ fraction containing xylenes is removed from the bottom of reactive distillation column 35 via line 47 and further separated and converted in xylene loop 49 to the desired molecules, e.g., para-xylene and other by-products.

Figure 2:
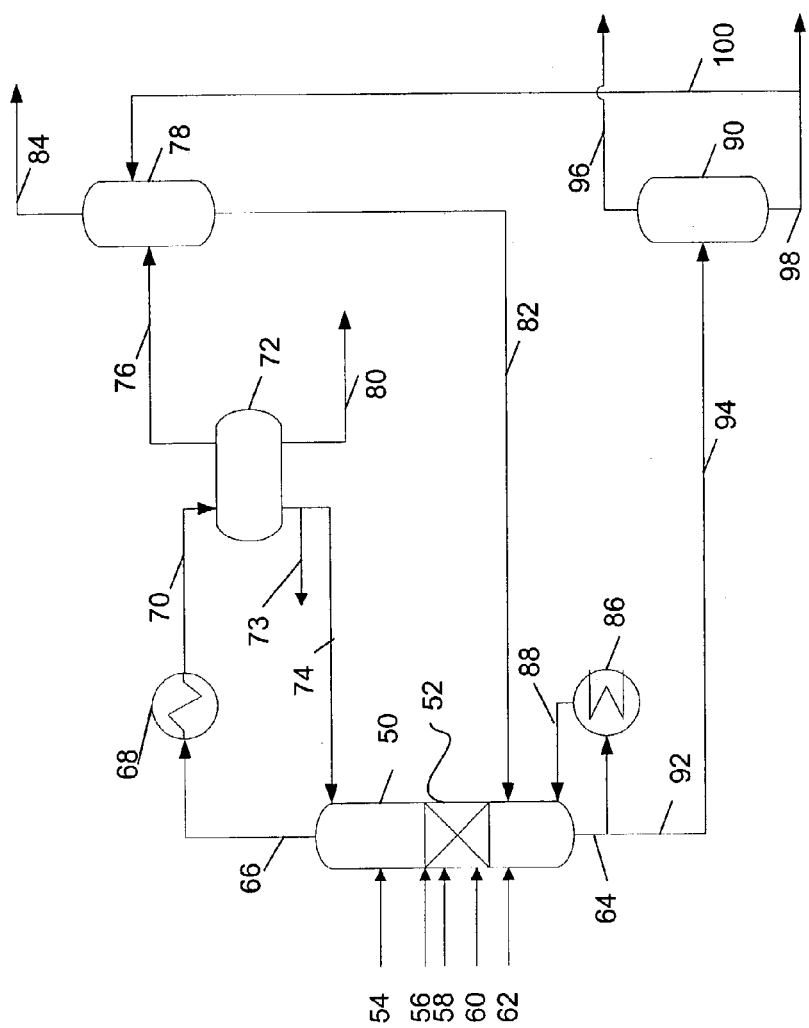
FIG. 2 illustrates a reactive distillation column with reboiler, condenser and other associated equipment that finds particular application in practicing the invention.

FIG. 2 illustrates a reactive distillation column with reboiler, condenser and other associated equipment that finds particular application in practicing of the invention. Referring to FIG. 2, reactive/distillation column 50 is provided with reaction section 52, inlet for toluene and/or benzene-containing feed 54, inlets for the methylating agent feed, 56, 58, 60, and 62, column bottom outlet line 64, and column overhead outlet line 66. Condenser 68 is connected to overhead outlet line 66. Condenser outlet line 70 is connected to separator drum 72. Separator drum 72 is provided with exit line 74 through which hydrocarbons are returned to reactive/distillation column 50 and line 73 where benzene or toluene-depleted material can be removed. Separator drum overhead product take-off line 76 is connected to scrubber 78. Separator drum 72 is equipped with water take-off line 80. Scrubber 78 is provided with exit line 82 through which a light hydrocarbon enriched stream can be returned to reactive/distillation column 50. Light gases exit through scrubber 78 through overhead take-off line 84.

Reboiler 86 is provided with line 88 through which xylenes rich product can be returned to reactive/distillation column 50. Xylenes product not sent back to reactive/distillation column 50 is sent to fractionator 90 via line 92 and line 94. Fractionator 90 is provided with overhead line 96 where xylenes are removed. $C_{9+}$ aromatics are removed via bottoms line 98 part of which is sent to scrubber 78 via line 100 to scrub $C_{6+}$ hydrocarbons from the product gas.

The catalyst bed is preferably located in the enriching section of reactive/distillation column 50. Catalyst used for methylation can be any catalyst effective for toluene/benzene methylation, e.g., catalyst that produces equilibrium amounts of para-xylene, or one that is selective to produce greater than equilibrium amounts of a desired xylene isomer, e.g., para-xylene. Reformate feed is usually added through inlet 54 at the top of the catalyst bed. However, if a large amount of refluxed liquid is present in the reactive/distillation column, reformate feed can also be added through inlets located at the bottom of the catalyst bed. The toluene/benzene in the feed serves as both a reactant and a heat sink. As toluene/benzene in the feed trickles down the bed, the liquid toluene/benzene will vaporize due to the heat of reaction allowing close to isothermal operation within the reaction zone. Excess toluene is separated from the xylenes within the stripping section of the reactive/distillation column 50 and is returned to the reaction zone as vapor. Condenser 78 condenses most of the $C_{6+}$ hydrocarbons, which usually will be primarily $C_6$–$C_7$ hydrocarbons containing toluene and benzene. A portion of the condensed liquids are then refluxed via line 74 to reactive/distillation column 50 except for water, which is drawn off from separator drum 72 as a separate stream via line 80.

The methylating agent (e.g. methanol, DME, syngas, etc.) is preferably injected into reactive/distillation column 50 via line 62 below the catalyst bed and preferably through a plurality of lines. FIG. 2 shows four lines as a non-limiting example, lines 56, 58, 60, and 62 within reactive/distillation column 50 at or near the reaction section containing the catalyst bed. Multiple injections can keep the methylating agent concentration low at points within the catalyst bed so as to reduce all reactions other than toluene methylation and to achieve nearly complete conversion of methanol. Methanol can be injected as either a vapor or liquid depending upon if methanol vaporization is desirable as a means of absorbing heat released in the toluene methylation reaction. It is desirable to have substantially all of the methanol, e.g., 99 percent or greater, converted within the catalyst bed. If methanol is only partially converted, it can be separated out of the reactive/distillation column overhead stream along with dimethyl-ether (DME) which may also be produced in small quantities. The overhead DME and methanol can then be recycled to extinction back to reactive/distillation column 50. The concentration of DME within the catalyst bed will eventually build to the point that it is catalytically consumed at the same rate as it is catalytically produced.

Reactive/distillation column 50 is preferably designed so that the pressure and temperature of the column is such that the reaction section will contain both liquid and gas phase xylenes and toluene. The concentration of xylenes within the reaction section will usually be much lower than the concentration of xylenes in other sections of reactive/distillation column 50 because xylenes product is constantly removed from reactive/distillation column 50 while toluene and/or benzene are continuously fed to the reaction section and refluxed. Liquid phase xylenes and toluene within the reaction section of the reactive/distillation column can enable coke precursors formed on the surface of the catalyst to be "washed away" thereby extending catalyst cycle length. Also, hydrogen can be added below the catalyst bed to help extend catalyst cycle length. Operating conditions and methylating agent injection points are preferably chosen so as to obtain high methylating agent conversion to xylenes. Since there should be low xylenes concentration within the reaction section, formation of undesirable by-products via xylenes transalkylation or xylenes methylation should be much lower than achievable in a fixed bed reactor at comparable process conditions.

Reactive/distillation column 50 is preferably designed to condense most of the xylenes entering the top zone by contact/heat exchange with refluxed toluene. Preferably, the column is designed so that the catalyst bed operates nearly isothermally. Isothermal operations are beneficial as they serve to extend catalyst life and allow operations at an optimum reaction temperature. Since toluene methylation is exothermic, it usually will be necessary to remove reaction heat. This can be accomplished by vaporizing feed and refluxing unreacted material.

Practicing the invention according to the embodiment shown in FIG. 1 allows sharing of both the benzene/toluene recovery unit and xylenes recovery unit. Also, since reduced amounts of toluene and benzene need to be recovered, the benzene/toluene recovery unit is debottlenecked. Further, practicing selective toluene methylation to produce para-xylene results in debottlenecking of the xylenes recovery unit.

Figure 3:
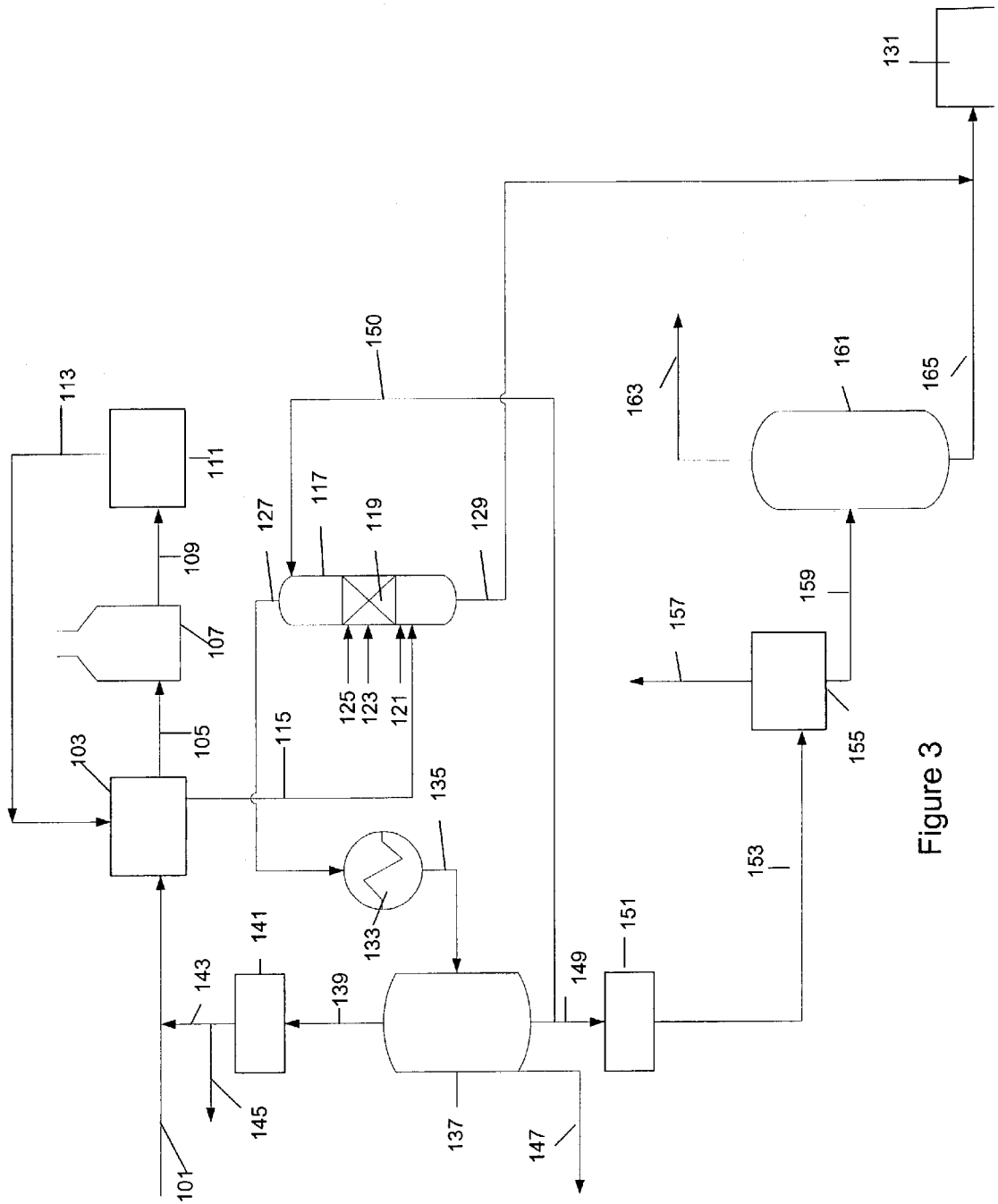
FIG. 3 is a simplified process flow diagram, illustrating a another embodiment of the invention.

FIG. 3 shows an embodiment of the invention where reformate methylation is carried out in a reactive/distillation column located inside of the reforming loop. Referring to FIG. 3, naphtha is directed via line 101 to heat exchanger 103 where the temperature of the naphtha is elevated. The naphtha feed can be either naphtha alone or the naphtha can be combined with toluene and/or benzene. Next, the heated naphtha is sent via line 105 to reformer heater 107 which elevates the temperature of the feed to a temperature suitable for reforming. After heating, the naphtha is withdrawn via line 109 to aromatization reactor zone 111 where the naphtha is partially reformed into aromatic products. Although only one reactor zone is shown, there can be more than one reactor zone. The reformate is then withdrawn through line 113 to heat exchanger 103 which cools the reformate product and uses heat recovered from the reformate to elevate the temperature of the naphtha supplied via line 101.

Next, the reformate is supplied via line 115 to reactive/distillation column 117 at a location below the catalyst bed. Although not shown, the reactive/distillation column will preferably include the condenser, reboiler, and other associated equipment shown in FIG. 2 and previously discussed. The methylation reaction can be carried out in the vapor phase. When carried out in the vapor phase, the reformate can be heated either before it enters the methylation reaction zone or after it has entered the methylation reaction zone. In reactive distillation column 117, toluene present in the reformate is methylated to form xylenes. Also, benzene present in the reformate can be methylated to form toluene which, in turn, can be methylated to form xylenes. Depending upon the composition of the reformate, other reactions may also occur. For example, ethylbenzene can be methylated to form para-ethyl-methylbenzene or dealkylated to form benzene, which in turn, can be methylated to form toluene which can be methylated to form xylenes. Also, any ethyl-methyl-benzene present in the reformate can be dealkylated to form toluene, which can be methylated to form xylenes. If desired, a stream of hydrocarbons comprised of benzene and/or toluene can be added to the reformate. Reactive/distillation column 117 is provided with reaction section 119, a plurality of inlets for the methylating agent feed, lines 121, 123, and 125 which is a non-limiting example, column overhead outlet line 127 and column bottoms outlet line 129. The methylating agent is preferably injected into reactive/distillation column 117 via line 121 below the catalyst bed and preferably through a plurality of lines. FIG. 3 shows, as a non-limiting example, three inlets, e.g., lines 121, 123, and/or 125. The $C_{8+}$ fraction containing xylenes is removed from the bottom of reactive distillation column 117 via line 129 and further separated and converted in xylene loop 131 to the desired molecules. The $C_7$– fraction, including benzene and toluene, are removed overhead via line 127 to heat exchanger 133 to cool the $C_7$– fraction for separation of hydrogen from the fraction. Next, the cooled fraction is sent via line 135 to high pressure separator 137 where hydrogen is recovered. Hydrogen is removed via line 139 and sent to water dryer/oxygenate removal unit 141. It is important that the water and oxygenates not be recycled with the hydrogen into aromatization reaction zone 111. Hydrogen is removed from unit 141 via line 143 and either recycled back to the reforming unit or removed from the system via line 145. Free water present in the methylated product can be removed from high pressure separator 137 via line 147. Next, the product is sent via line 149 to dryer 151 where remaining water and oxygenates are removed. Alternatively, at least a portion of the product can be sent via line 150 to reactive distillation column 117 as a reflux where the benzenes and toluenes present in the product can be converted to xylenes. The product is then sent via line 153 to separation block 155 where low pressure hydrogen, $C_{4-}$ and $C_5$ are separated and removed via line 157. The resulting product, $C_{6+}$, is transferred via line 159 to distillation column 161 where $C_6/C_7$, including benzene and toluene, are removed overhead via line 163 for further processing or sent to reactive distillation column 117. The $C_{8+}$ fraction is removed from the bottom of distillation column 161 via line 165 and further separated and converted in xylene loop 131 to the desired molecules, e.g., para-xylene and other by-products. Practicing of the invention according to this embodiment allows sharing of the heat exchangers, furnace, compressor, phase separator distillation, and the extraction hardware.

Aromatization

Aromatization will usually be carried out by catalytic reforming of naphtha or the dehydrocyclo-oligomerization of $C_2$–$C_5$ aliphatics.

Dehydrocyclo-oligomerization involves converting $C_2$–$C_5$ aliphatic hydrocarbons to aromatic hydrocarbons. The process is carried out by contacting $C_2$–$C_5$ aliphatic hydrocarbons in an aromatization zone and in the presence of a catalyst suitable for dehydrocyclodimerization and under conditions effective to produce a aromatics product comprising benzene and/or toluene. The dehydrocyclodimerization process increases carbon chain length by oligomerization, promotes cyclization, and dehydrogenates cyclics to their respective aromatics.

The feedstream used in the dehydrocyclo-oligomerization process will contain at least one aliphatic hydrocarbon containing 2 to about 5 carbon atoms. The aliphatic hydrocarbons may be open chain, straight chain, or cyclic. Examples such as hydrocarbons include ethane, ethylene, propane, propylene, n-butane, n-butenes, isobutane, isobutene, butadiene, straight and branch pentane, pentene, and pentyldiene. Dehydrocyclo-oligomerization conditions will vary depending on such factors as feedstock composition and desired conversion. A desired range of conditions for the dehydrocyclodimerization of the aliphatic hydrocarbons to aromatics include a temperature from about 350° to about 650° C., a pressure from about 1 to about 100 atmospheres, and weight hour space velocity from about 0.2 to about 8. It is understood that, as the average carbon number of the feed increases, a temperature in the lower end of temperature range is required for optimum performance and conversely, as the average carbon number of the feed decreases, the higher the required reaction temperature.

The catalyst used in the dehydrocyclo-oligomerization reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type molecular sieves. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11, as well as titanosilicate, gallosilicate, aluminosilicate, and gallium-containing aluminosilicate molecular sieves having a MFI structure.

Usually the molecular sieve will be combined with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642, which is hereby incorporated by reference.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 20 to about 50 percent.

To make enhanced amounts (greater than equilibrium amounts) of para-xylene (versus the other xylene isomers produced by the dehydrocyclo-oligomerization reaction), a molecular sieve catalyst, e.g., ZSM-5 catalyst, can be selectivated by the use of a selectivating agent.

Examples of compounds for selectivating the catalysts include treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide.

Selectivation may also be accomplished by depositing coke on the catalyst. The coke selectivation can be carried out during the methylation reaction such as by running the methylation reaction at conditions which allow the deposition of coke on the catalyst. Also, the catalyst can be preselectivated with coke such as by exposing the catalyst in the reactor to a thermally decomposable organic compound, e.g., benzene, toluene, etc. at a temperature in excess of the decomposition temperature of said compound, e.g., from about 400° C. to about 650° C., more preferably 425° C. to about 550° C., at a WHSV in the range of from about 0.1 to about 20 lbs. of feed per pound of catalyst per hour, at a pressure in the range of from about 1 to about 100 atmospheres, and in the presence of 0 to about 2 moles of hydrogen, more preferably from about 0.1 to about 1 moles of hydrogen per mole of organic compound, and optionally in the presence of 0 to about 10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke.

Selectivation of the catalyst may also be accomplished using organosilicon compounds. The silicon compounds may comprise a polysiloxane include silicones, a siloxane, and a silane including disilanes and alkoxysilanes.

Silicone compounds that can be used in the present invention include the following:

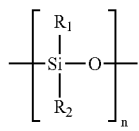

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclo-trisiloxane, octaethylcyclo tetrasiloxane, hexaphenylcyclotrisiloxane and octaphenylcyclotetrasiloxane.

Useful silanes, disilanes, or alkoxysilanes include organic substituted silanes having the general formula:

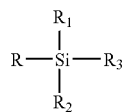

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenylrimethylsilane, triethylsilane and hexamethyldislane. Useful alkoxysilanes are those with at least one silicon-hydrogen bond.

Selectivation of the catalyst can also be accomplished using a combination of coke and silicon applied by the procedures described above.

Catalytic reforming involves the production of aromatics from a $C_6+$ paraffinic feed, e.g., naphtha, by contacting the feed with a reforming catalyst under reforming conditions to produce a reaction product comprising aromatics and paraffins. The reformate is formed under typical reforming conditions designed to promote dehydrogenation of naphthenes, isomerization of paraffinic hydrocarbons and dehydrocyclization of non-aromatic hydrocarbons.

Catalysts suitable for use in catalytic reforming include acidic reforming catalysts (bifunctional catalysts) and non-acidic reforming catalysts (monofunctional catalysts).

Acidic reforming catalysts usually comprise a metallic oxide support having disposed therein a Group VIII metal. Suitable metallic oxide supports include alumina and silica. Preferably, the acidic reforming catalyst comprises a metallic oxide support having disposed therein in intimate admixture a Group VIII metal (preferably platinum) and a metal promoter, such as rhenium, tin, germanium, cobalt, nickel, iridium, rhodium, ruthenium and combinations thereof. More preferably, the acidic reforming catalyst comprises an alumina support, platinum, and rhenium or platinum and tin on an alumina support.

Non-acidic or monofunctional reforming catalysts will comprise a non-acidic molecular sieve, e.g., zeolite, and one or more hydrogenation/dehydrogenation components. Examples of suitable molecular sieves include MFI structure type, e.g., silicalite, and zeolites having a large pore size, e.g., pore size from about 7 to 9 Angstroms. Examples of large pore molecular sieves include LTL, FAU, and *BEA structure types. Examples of specific molecular sieves include zeolite L, zeolite X, zeolite Beta, zeolite Y, and ETS-10.

The non-acidic catalysts will contain one or more hydrogenation/dehydrogenation metals, e.g., Group VII B metals, such as rhenium, and Group VIII metals, such as nickel, ruthenium, rhodium, palladium, iridium or platinum. The preferred Group VIII metal is platinum. Also, the non-acidic catalysts can contain a metal promoter such as tin.

The amount of hydrogenation/dehydrogenation metal present on the non-acidic catalyst will usually be from about 0.1% to about 5% of hydrogenation/dehydrogenation metal based on the weight of the catalyst. The metal can incorporated into the zeolite during synthesis of the zeolite, by impregnation, or by ion exchange of an aqueous solution containing the appropriate salt. By way of example, in an ion exchange process, platinum can be introduced by using cationic platinum complexes such as tetraammine-platinum (II) nitrate.

The non-acidic catalyst will usually include a binder. The binder can be a natural or a synthetically produced inorganic oxide or combination of inorganic oxides. Typical inorganic oxide supports which can be used include clays, alumina, and silica, in which acidic sites are preferably exchanged by cations that do not impart strong acidity.

The reforming process can be continuous, cyclic or semi-regenerative. The process can be in a fixed bed, moving bed, tubular, radial flow or fluid bed.

Conditions for reforming conditions include temperatures of at least about 400° C. to about 600° C. and pressures from about 50 psig (446 kPa) to about 500 psig (3,549 kPa), a mole ratio of hydrogen to hydrocarbons from 0.1:1 to 10:1 and a liquid hour space velocity of between 0.3 and 10.

Substantially any hydrocarbon feed containing $C_{6+}$ e.g., naphtha can be utilized. The naphtha will generally comprise $C_6$–$C_9$ aliphatic hydrocarbons. The aliphatic hydrocarbons may be straight or branched chain acyclic hydrocarbons, and particulary paraffins such as heptane.

Toluene/Benzene Methylation

The term "reactive distillation", as used herein, means the production of xylenes while concurrently removing xylenes product from a reaction zone. The term "reactive/distillation column", as used herein, means a column in which toluene, benzene, or mixtures thereof present in the reformate is contacted in the presence of a toluene/benzene methylation catalyst to produce xylenes and from which the xylenes are withdrawn.

In a preferred embodiment, the process of the methylation reaction is carried out in a reactive/distillation column. In this embodiment, toluene, benzene, or mixtures thereof present in the reformate and the methylating agent are usually fed continuously to the reactive/distillation column and the xylenes are continuously withdrawn from the bottom of the reactive/distillation column. In this embodiment, the continuous removal of xylenes from the reactive/distillation column increases the extent of reaction achieved within the column, thus providing very high toluene/bemzene to xylenes conversion along with low by-product formation.

The invention can be practiced to result in significant conversion of benzene to toluene with minimal conversion of toluene to xylenes. To practice this embodiment, the reformate enters the reactive/distillation column below the catalyst bed, e.g., at least one bed below the catalyst bed, and the process is operated at a temperature such that minimum amounts of the toluene present in the feed would be vaporized and conducted up into the catalyst bed.

The reactive/distillation column will contain an enriching section that leads to the column overhead fine and a stripping section that leads to the column bottom outlet line. Internally, the column will contain a plurality of trays or theoretical distillation stages. The catalyst bed is preferably located in the enriching section.

Usually, the reactive/distillation column will employ a reboiler for returning to the reactive/distillation column at least a portion of the heated xylenes-enriched product withdrawn from the bottom of the reactive/distillation column. Also, the reactive/distillation column will usually employ a condenser for returning to the reactive/distillation column at least a portion of the product withdrawn from the top of the reactive/distillation column.

The process of the present invention is typically operated at a temperature no greater than about 320° C. and, preferably, from about 225° C. to about 300° C. However, the particular temperature is dependent upon a number of factors including, for example, the reactant flow rates, the operating pressure and the desired production rate. The molar ratio of toluene and benzene to methylating agent supplied for reactive distillation reaction will preferably be greater than 0.5 and, more preferably, greater than about 1. Hydrogen gas can be supplied to the reaction as an anticoking agent and diluent. The methylating agent is usually supplied to the reaction zone through multiple feed points, e.g., 3–6 feed points.

Typical methylating agents include methanol, dimethylether, methylchloride, methylbromide, methylcarbonate, acetaldehyde, dimethoxyethane, acetone, and dimethylsulfide. The methylating agent can also be formed from synthesis gas, e.g., the agent can be formed from the $H_2$, CO, and/or $CO_2$ of synthesis gas. The methylating agent can be formed from the synthesis gas within the reactive/distillation zone. One skilled in the art will know that other methylating agents may be employed to methylate the benzene and/or toluene based on the description provided therein. Preferred methylating agents are methanol and dimethylether. Methanol is most preferred.

Catalysts suitable for use in the present invention include any catalyst that is effective for toluene or benzene methylation. The catalyst used in the process will usually comprise a crystalline molecular sieve.

The catalyst used in the methylation reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type molecular sieves. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11 as well as titanosilicate, gallosilicate, aluminosilicate, and gallium-containing aluminosilicate molecular sieves having a MFI structure.

The intermediate pore size molecular sieve will generally be a composition having the following molar relationship:

$$X_2O_3:(n)YO_2,$$

wherein X is a trivalent element such as titanium, aluminum, iron, boron, and/or gallium and Y is a tetravalent element such as silicon, tin, and/or germanium; and n has a value greater than 12, said value being dependent upon the particular type of molecular sieve. When the molecular sieve has a MFI structure type molecular sieve, n is preferably greater than 10 and preferably, from 20:1 to 200:1.

When the molecular sieve is a gallium silicate molecular sieve, the molecular sieve usually will be a composition having the following molar relationship:

$$Ga_2O_3:ySiO_2$$

wherein y is between about 20 and about 500. The molecular sieve framework may contain only gallium and silicon atoms or may also contain a combination of gallium, aluminum, and silicon.

Usually the molecular sieve will be incorporated with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 20 to about 50 percent.

The catalyst may also include at least one hydrogenation/dehydrogenation metal. Such metals can reduce the rate of deactivation of the catalyst. Reference to hydrogenation/dehydrogenation metal or metals is intended to encompass such metal or metals in the elemental state (i.e. zero valent) or in some other catalytically active form such as an oxide, sulfide, halide, carboxylate and the like. Such metals are known to persons skilled in the art and include, for example, one or more metals, and metals of Groups IIIA, IVA, VA, VIA, VIIA, VIII, IB, IIB, IIIB, IVB, VB, VIB, and VB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are sometimes preferred.

When the catalyst used for the methylation reaction is a molecular sieve, the catalyst can be selectivated to enhance the amount of para-xylene produced by the methylation reaction by the use of a selectivating agent. Suitable selectivating agents include the selectivating agents disclosed earlier in this application for selectivating dehydrocyclo-oligomerization molecular sieve catalysts.

Catalysts particularly suited for the methylation reaction include zeolite bound zeolite catalysts. These catalysts, as well as their method of preparation, are described in U.S. Pat. No. 5,994,603, which is hereby incorporated by reference. The zeolite bound zeolite catalysts will comprise first crystals of an acidic intermediate pore size first molecular sieve and a binder comprising second crystals of a second molecular sieve. Preferably, the zeolite bound zeolite catalyst contains less than 10 percent by weight based on the total weight of the first and second zeolite of non-zeolitic binder, e.g., amorphous binder. An example of such a catalyst comprises first crystals of a MFI or MEL structure type, e.g., ZSM-5 or ZSM-11, and a binder comprising second crystals of MFI or MEL structure type, e.g., Silicalite 1 or Silicalite 2.

The amount of benzene/toluene converted to xylenes will depend on a number of factors including the make up of the reformate to be methylated, the methylation conditions, and the catalyst used. Usually, at least 5 weight percent of the benzene/toluene will be converted to xylenes. Preferably, at least 7 weight percent of the benzene/toluene will be converted to xylenes, and, more preferably, at least 30 weight percent of the benzene/toluene will be converted to xylenes.

The process of the present invention of methylation of the benzene, toluene, or mixtures thereof present in the reformate can produce greater than equilibrium amounts of para-xylene. Preferably, the process will produce a xylene product containing greater than 30 weight percent para-xylene based on the total weight of xylenes produced by the process. More preferably, the process produces a xylene product containing greater than 60 weight percent para-xylene based on the total weight of the xylenes produced by the process. Most preferably, the process produces a xylene product containing greater than 80 weight percent para-xylene based on the total weight of the xylenes produced by the process.

The invention is further exemplified by the examples below, which are present to illustrate certain specific embodiments of the invention, but are not intended to be construed as to be restrictive of the spirit and scope thereof.

EXAMPLE 1

The following example is a computer simulation of reformate methylation by the process of the present invention. A simulated full range reformate is used as the feed in this example.

Simulation results were obtained using Pro II Version 5.5 Software from Simulation Services Inc. Vapor pressure measurements were converted into equilibrium vapor and liquid compositions using an activity coefficient model, i.e., the Non-Random, Two-Liquid (NRTL) method.

Reaction stoichiometry used for the simulation was the following:

2 Methanol→1 Ethylene+2H$_2$O

Methanol+Toluene→Xylene

Methanol+Benzene→Toluene

C$_6$H$_{14}$+5H$_2$→6 Methane

C$_8$H$_{18}$+7H$_2$→8 Methane

In the process simulation, the reaction proceeds in a reactive/distillation column similar to the reactive/distillation column shown in FIG. 2. A fifty seven theoretical distillation stage reactive/distillation column is used in the simulation. The distillation stages are identified by their order from top Stage 1 while the bottom stage is Stage 57. Stages between Stage 1 and Stage 57 are identified using this numbering sequence. The reformate methylation catalyst used for the simulation is H-ZSM-5 that is not selectivated. The catalyst is located in stage 28 through 29 (below the toluene feed [stage 27] and above the methanol feed [stage 30]). In the simulation, it is assumed the catalyst will convert 100% of the methanol.

The pressure of the reactive/distillation column is 90 psia. A reboiler and condenser are connected to the reactive/distillation column similar to the conections to reboiler and condenser shown in FIG. 2. The heat input of the reboiler and the condenser duty was determined by criteria of separation whereby overhead product would contain less than 0.25% para-xylene.

Table 1 below summarizes the stream component flow rates. The methanol feed and the reformate feed compositions along with the temperature and pressure conditions are listed below in Table 1. All flow rates are in Pound-Mole/Hour.

TABLE 1

| Stream Description Phase | Reformate Feed Liquid | Methanol Vapor | Bottom Liquid | Overhead Vapor |
|---|---|---|---|---|
| Temperature (° F.) | 363.000 | 363.000 | 408.925 | 250.110 |
| Pressure (psia) | 94.696 | 94.000 | 88.250 | 79.696 |
| Molecular Weight | 91.475 | 8.290 | 101.628 | 31.769 |
| Components | Flow Rate | Flow Rate | Flow Rate | Flow Rate |
| Hexane | 2.000 | | 0.000 | 1.600 |
| Octane | 2.000 | | 0.070 | 0.330 |
| Benzene | 15.000 | | 0.000 | 13.500 |
| Toluene | 50.000 | | 5.379 | 42.372 |
| Ethylbenzene | 1.000 | | 0.744 | 0.256 |
| Ortho-xylene | 2.000 | | 2.888 | 0.056 |
| Meta-xylene | 4.000 | | 4.996 | 0.869 |
| Para-xylene | 2.000 | | 2.423 | 0.517 |
| Methanol | | 28.000 | 0.000 | 0.204 |
| Hydrogen | | 106.000 | 0.000 | 92.800 |
| Water | | | 0.000 | 27.796 |
| Methane | | | 0.000 | 15.200 |
| Ethylene | | | 0.000 | 11.274 |
| Total (LB-MOL/HR) | 78.000 | 134.000 | 16.500 | 206.773 |

The results in Table 1 show conversion of benzene/toluene present in the reformate to xylenes. The percentage of para-xylene to total xylenes in the final product is about 25%.

EXAMPLE 2

A computer simulation is carried out in the same manner as Example 1, except that the reformate methylation catalyst is H-ZSM-5 that is slightly selectivated with coke, and the feed is steam cracking reformate.

Table 2 below summarizes the stream component flow rates. The methanol feed and the reformate feed compositions along with the temperature and pressure conditions are listed below in Table 2. All flow rates are in Pound-Mole/Hour.

TABLE 2

| Stream Description Phase | Reformate Feed Liquid | Methanol Vapor | Bottom Liquid | Overhead Vapor |
|---|---|---|---|---|
| Temperature (° F.) | 363.000 | 363.000 | 409.779 | 249.721 |
| Pressure (psia) | 94.696 | 94.000 | 88.250 | 79.696 |
| Molecular Weight | 91.475 | 8.290 | 101.843 | 31.752 |
| Components | Flow Rate | Flow Rate | Flow Rate | Flow Rate |
| Hexane | 2.000 | | 0.000 | 1.600 |
| Octane | 2.000 | | 0.069 | 0.331 |
| Benzene | 15.000 | | 0.000 | 13.500 |
| Toluene | 50.000 | | 5.126 | 42.624 |
| Ethylbenzene | 1.000 | | 0.770 | 0.230 |
| Ortho-xylene | 2.000 | | 2.716 | 0.034 |
| Meta-xylene | 4.000 | | 4.836 | 0.664 |
| Para-xylene | 2.000 | | 2.983 | 0.517 |
| Methanol | | 28.000 | 0.000 | 0.204 |
| Hydrogen | | 106.000 | 0.000 | 92.800 |
| Water | | | 0.000 | 27.796 |
| Methane | | | 0.000 | 15.200 |
| Ethylene | | | 0.000 | 11.273 |
| Total (LB-MOL/HR) | 78.000 | 134.000 | 16.500 | 206.773 |

The results in Table 2 show conversion of benzene/toluene present in the reformate to xylenes. The percentage of para-xylene to total xylenes in the final product is about 30%, which is greater than an equilibrium amount (24% para-xylene).

EXAMPLE 3

A computer simulation is carried out in the same manner as Example 1, except that the reformate methylation catalyst is silica-selectived H-ZSM-5 and the feed is steam cracking reformate.

Table 3 below summarizes the stream component flow rates. The methanol feed and the reformate feed compositions along with the temperature and pressure conditions are listed below in Table 3. All flow rates are in Pound-Mole/Hour.

TABLE 3

| Stream Description Phase | Reformate Feed Liquid | Methanol Vapor | Bottom Liquid | Overhead Vapor |
|---|---|---|---|---|
| Temperature (° F.) | 363.000 | 363.000 | 384.433 | 224.755 |
| Pressure (psia) | 94.696 | 94.000 | 88.250 | 79.696 |
| Molecular Weight | 85.181 | 8.290 | 97.564 | 29.780 |
| Components | Flow Rate | Flow Rate | Flow Rate | Flow Rate |
| Hexane | 2.000 | | 0.000 | 1.600 |
| Octane | 2.000 | | 0.123 | 0.277 |
| Benzene | 15.000 | | 2.523 | 42.477 |
| Toluene | 50.000 | | 5.145 | 13.730 |
| Ethylbenzene | 1.000 | | 0.751 | 0.249 |
| Ortho-xylene | 2.000 | | 2.038 | 0.037 |
| Meta-xylene | 4.000 | | 3.536 | 0.614 |
| Para-xylene | 2.000 | | 2.384 | 0.516 |
| Methanol | | 28.000 | 0.000 | 0.168 |
| Hydrogen | | 106.000 | 0.000 | 92.800 |
| Water | | | 0.000 | 27.832 |
| Methane | | | 0.000 | 15.200 |
| Ethylene | | | 0.000 | 10.853 |
| Total (LB-MOL/HR) | 78.000 | 134.000 | 16.500 | 206.773 |

The results in Table 3 show conversion of benzene/toluene present in the reformate to xylenes. The percentage of para-xylene to total xylenes in the final product is about 32%, which is greater than an equilibrium amount.

EXAMPLE 4

A computer simulation was carried out for the process of the present invention. The simulation is carried out in the same manner as Example 1, except that the reformate methylation catalyst is H-ZSM-5 that is slightly selectivated with coke, and the feed is reformate formed by the dehydrocyclo-oligomerization of $C_2$–$C_5$ aliphatic hydrocarbons.

Table 4 below summarizes the stream component flow rates. The methanol feed and the reformate feed compositions along with the temperature and pressure conditions are listed below in Table 4. All flow rates are in Pound-Mole/Hour.

TABLE 4

| Stream Description | Reformate Feed | Methanol | Bottom | Overhead |
|---|---|---|---|---|
| Phase | Liquid | Vapor | Liquid | Vapor |
| Temperature (° F.) | 363.000 | 363.000 | 408.214 | 246.435 |
| Pressure (psia) | 94.696 | 94.000 | 88.250 | 79.696 |
| Molecular Weight | 90.576 | 8.290 | 101.515 | 31.448 |
| Components | Flow Rate | Flow Rate | Flow Rate | Flow Rate |
| Hexane | 2.000 | | 0.000 | 1.600 |
| Octane | 2.000 | | 0.075 | 0.325 |
| Benzene | 20.000 | | 0.000 | 18.000 |
| Toluene | 45.000 | | 5.515 | 38.110 |
| Ethylbenzene | 1.000 | | 0.764 | 0.236 |
| Ortho-xylene | 2.000 | | 2.639 | 0.036 |
| Meta-xylene | 4.000 | | 4.672 | 0.678 |
| Para-xylene | 2.000 | | 2.833 | 0.517 |
| Methanol | | 28.000 | 0.000 | 0.199 |
| Hydrogen | | 106.000 | 0.000 | 92.800 |
| Water | | | 0.000 | 27.801 |
| Methane | | | 0.000 | 15.200 |
| Ethylene | | | 0.000 | 11.213 |
| Total (LB-MOL/HR) | 78.000 | 134.000 | 16.500 | 206.773 |

The results in Table 4 show conversion of benzene/toluene present in the reformate to xylenes. The percentage of para-xylene to total xylenes in the final product is about 29%, which is greater than an equilibrium amount.

EXAMPLE 5

A computer simulation was carried out for the process of the present invention. The simulation is carried out in the same manner as Example 1, except that the reformate methylation catalyst is a silica-selectivated H-ZSM-5. The feed used is full range naphtha reformate.

Table 5 below summarizes the stream component flow rates. The methanol feed and the reformate feed compositions along with the temperature and pressure conditions are listed below in Table 5. All flow rates are in Pound-Mole/Hour.

TABLE 5

| Stream Description | Reformate Feed | Methanol | Bottom | Overhead |
|---|---|---|---|---|
| Phase | Liquid | Vapor | Liquid | Vapor |
| Temperature (° F.) | 363.000 | 363.000 | 410.871 | 249.194 |
| Pressure (psia) | 94.696 | 94.000 | 88.250 | 79.696 |
| Molecular Weight | 91.475 | 8.290 | 102.158 | 31.736 |
| Components | Flow Rate | Flow Rate | Flow Rate | Flow Rate |
| Hexane | 2.000 | | 0.000 | 1.600 |
| Octane | 2.000 | | 0.068 | 0.332 |
| Benzene | 15.000 | | 0.000 | 13.500 |
| Toluene | 50.000 | | 4.756 | 42.994 |
| Ethylbenzene | 1.000 | | 0.816 | 0.184 |
| Ortho-xylene | 2.000 | | 2.237 | 0.013 |
| Meta-xylene | 4.000 | | 4.141 | 0.359 |
| Para-xylene | 2.000 | | 4.483 | 0.517 |
| Methanol | | 28.000 | 0.000 | 0.324 |
| Hydrogen | | 106.000 | 0.000 | 92.800 |
| Water | | | 0.000 | 27.676 |
| Methane | | | 0.000 | 15.200 |
| Ethylene | | | 0.000 | 11.213 |
| Total (LB-MOL/HR) | 78.000 | 134.000 | 16.500 | 206.773 |

The results in Table 5 show conversion of benzene/toluene present in the reformate to xylenes. The percentage of para-xylene to total xylenes in the final product is about 43%, which is greater than an equilibrium amount.

What is claimed is:

1. A process for producing xylenes from reformate, which process comprises:
   (a) forming a full range naphtha reformate containing benzene, toluene or mixtures thereof and hydrogen; and,
   (b) methylating at least a portion of the benzene, toluene, or mixtures thereof present in said full range naphtha reformate in a reactive distillation zone with a methylating agent in the vapor phase and under reactive/distillation conditions and in the presence of a catalyst effective for the methylation and comprising a silica selectivated ZSM-5 molecular sieve molecular sieve to produce a resulting product having a higher xylenes content than said reformate;
   wherein said full range naphtha reformate is transferred to said methylation reaction zone without interstage separation.

2. The process recited in claim 1, wherein the temperature of said reformate transferred to said reactive distillation zone is sufficient for methylating benzene and toluene.

3. The process recited in claim 1, wherein said catalyst further comprises at least one hydrogenation/dehydrogenation metal.

4. The process recited in claim 3, wherein said at least one hydrogenation/dehydrogenation metal is a Group VIII metal.

5. The process recited in claim 1, wherein said reformate is formed by the cracking of hydrocarbons.

6. The process recited in claim 5, wherein said cracking of hydrocarbons is accomplished in a catalytic cracking process.

7. The process recited in claim 5, wherein said cracking of hydrocarbons is accomplished in a steam cracking process.

8. The process recited in claim 1, wherein said molecular sieve further comprises another selectivating agent.

9. The process recited in claim 8, wherein said a selectivating agent is selected from the group consisting of coke, phosphorus, alkaline earth metal oxide, rare earth metal oxides, lanthanum oxide, boron oxide, titania, antimony oxide, manganese oxide, titania and mixtures thereof.

10. The process recited in claim 9, wherein said process produces a para-xylene product of greater 30 weight percent based on the total weight of the xylenes produced by the process.

11. The process recited in claim 9, wherein wherein said resulting product contains greater than 80 weight percent of para-xylene based on the total weight of the xylenes produced in said methylation reaction zone by the methylation of said benzene, toluene, or mixtures thereof.

12. The process recited in claim 1, wherein said reactive distillation zone comprises a reactive/distillation column.

13. The process recited in claim 12, wherein said reactive/distillation column contains a reactor section and said methylating agent is supplied to said reactive/distillation column at a location below the catalyst bed.

14. The process recited in claim 12, wherein a xylenes-enriched product is withdrawn from the bottom of said reactive/distillation column and at least a portion of said xylenes-enriched product is returned to said reactive/distillation column.

15. The process recited in claim 14, wherein a product is withdrawn from the top of said reactive/distillation column and at least a portion of said product is returned to said reactive/distillation column.

16. The process recited in claim 12, wherein said methylating agent is selected from the group consisting of methanol, dimethylether, methylchloride, methylbromide, methylcarbonate, acetaldehyde, dimethoxyethane, acetone, and dimethylsulfide.

17. The process recited in claim 12, wherein said methylating agent is formed from synthesis gas.

18. The process recited in claim 12, wherein said methylating agent is formed from synthesis gas in said reactive/distillation column.

19. The process recited in claim 12, wherein reformate contains ethylbenzene, ethyl-methyl-benzene, or mixtures thereof and at least a portion of said ethylbenzene or ethyl-methyl-benzene is dealkylated in said reactive distillation zone to form toluene or benzene.

20. A process recited in claim 1, wherein said full range naphtha reformate is formed in an aromatization zone.

21. The process recited in claim 20, wherein a hydrocarbon stream comprising benzene, toluene, or mixtures thereof is added to said reformate.

22. The process recited in claim 20, wherein hydrogen is supplied to said reactive distillation zone.

23. The process recited in claim 20, wherein at least 7 weight percent of the benzene and/or toluene present in said reformate is converted to xylenes.

24. The process recited in claim 20, further comprising recovering said xylenes from said resulting product.

25. The process recited in claim 20, wherein said reactive/distillation conditions include a temperature no greater than about 320° C.

26. The process recited in claim 25, wherein said temperature is in the range of from about 225° C. to about 300° C.

27. The process recited in claim 25, wherein substantially all of the methylating agent is consumed.

28. The process recited in claim 25, wherein said molar ratio of toluene and benzene to methylating agent is greater than about 1.

29. The process recited in claim 28, wherein said methylating agent is injected continuously into said reactive/distillation column.

30. The process recited in claim 29, wherein said methylating agent is injected into said reactive/distillation column at a plurality of injection points.

31. The process recited in claim 20, wherein said reformate is formed by the catalytic reforming of naphtha.

32. The process recited in claim 31, wherein said reforming is carried out a temperature in the range of from about 427° C. to about 565° C., a pressure in the range of from about 50 psig (446 kPa) to about 500 psig (3,549 kPa), a mole ratio of hydrogen to hydrocarbons from 0.1:1 to 10:1 and a liquid hour space velocity of between 0.3 and 5 and in the presence of a catalyst suitable for the catalytic reforming of naphtha.

33. The process recited in claim 32, wherein the catalyst used in said reforming is a bifunctional catalyst.

34. The process recited in claim 33, wherein said bifunctional catalyst is an acidic reforming catalyst comprising a metallic oxide support and a Group VIII metal.

35. The process recited in claim 34, wherein said metallic oxide support of said bifunctional catalyst is silica or alumina and said Group VIII metal is platinum.

36. The process recited in claim 34, wherein said bifunctional catalyst further comprises a metal promoter.

37. The process recited in claim 36, wherein said metal promoter is tin, rhenium, or mixtures thereof.

38. The process recited in claim 32, wherein the catalyst used in said reforming is a monofunctional catalyst.

39. The process recited in claim 38, wherein said monofunctional catalyst comprises a molecular sieve selected from the group consisting of zeolite L, zeolite X, zeolite Beta, zeolite Y, and ETS-10.

40. The process recited in claim 39, wherein said monofunctional catalyst further comprises from about 0.1 to about 5% of at least one hydrogenation/dehydrogenation metal selected from the group consisting of a Group VIII metal, a Group VIIB metal, and mixtures thereof, based on the weight of the catalyst.

41. The process recited in claim 40, wherein said monofunctional catalyst further comprises a metal promoter and said Group VIII metal is platinum.

* * * * *